United States Patent [19]

Danby et al.

[11] Patent Number: 4,537,387
[45] Date of Patent: Aug. 27, 1985

[54] PRECISION VALVE ASSEMBLY

[75] Inventors: Hal C. Danby, Palo Alto; Werner W. Ciupke, San Mateo, both of Calif.

[73] Assignee: Anatros Corporation, San Jose, Calif.

[21] Appl. No.: 431,311

[22] Filed: Sep. 30, 1982

[51] Int. Cl.³ .............................................. F16K 7/12
[52] U.S. Cl. .................................. 251/331; 251/61.1; 137/510
[58] Field of Search .................. 251/61.1, 6, 7, 8, 9, 251/10, 4, 5, 331, 205, 80; 137/210

[56] References Cited

U.S. PATENT DOCUMENTS

| 1,180,807 | 4/1916 | Vedder | 251/80 X |
| 3,011,758 | 12/1961 | McFarland | 251/331 |
| 3,511,472 | 5/1970 | Zimmerman | 251/331 |
| 3,984,081 | 10/1976 | Hoganson | 251/6 |
| 4,375,882 | 3/1983 | Schreiber, Jr. | 251/331 |

Primary Examiner—Alan Cohan
Attorney, Agent, or Firm—William B. Walker

[57] ABSTRACT

A precision valve assembly for controlling the flow of fluids delivered to a patient has a valve element mounted on a flexible diaphragm. A controlled actuator displaces a portion of the diaphragm surface, flexing it, and by a leverage action, moves the valve closer to or away from the valve seat.

7 Claims, 13 Drawing Figures

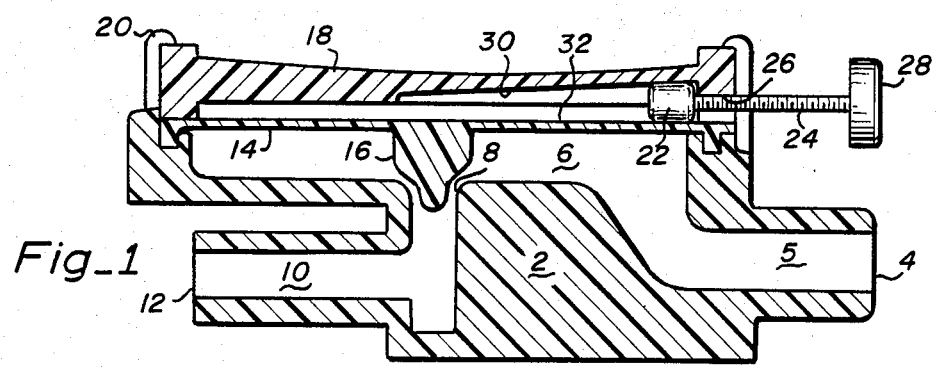
Fig_1
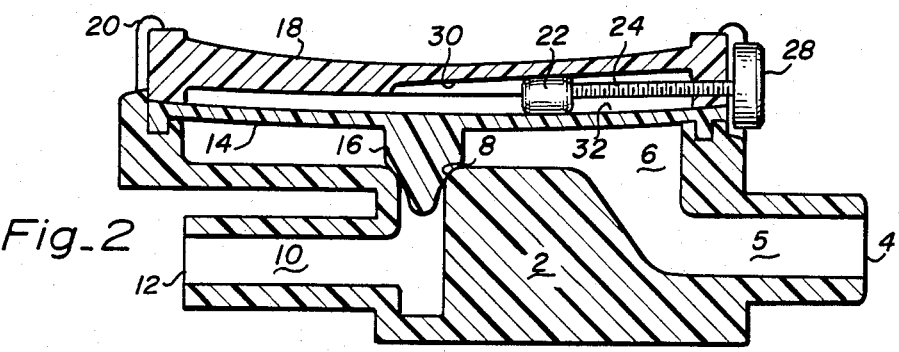
Fig_2
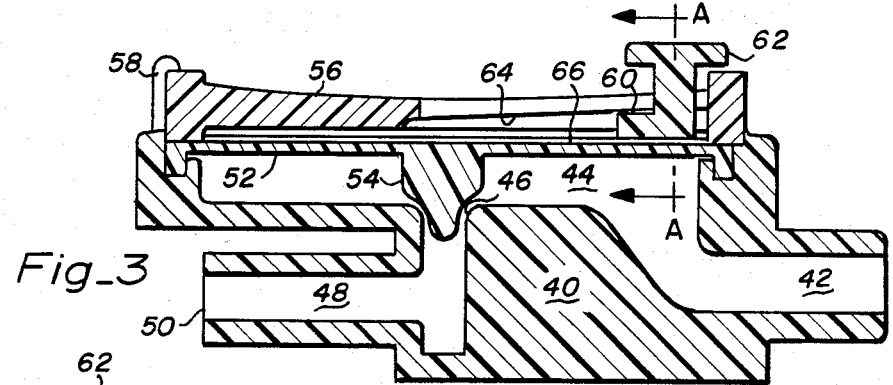
Fig_3
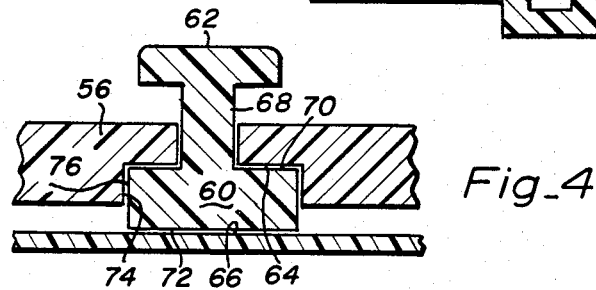
Fig_4
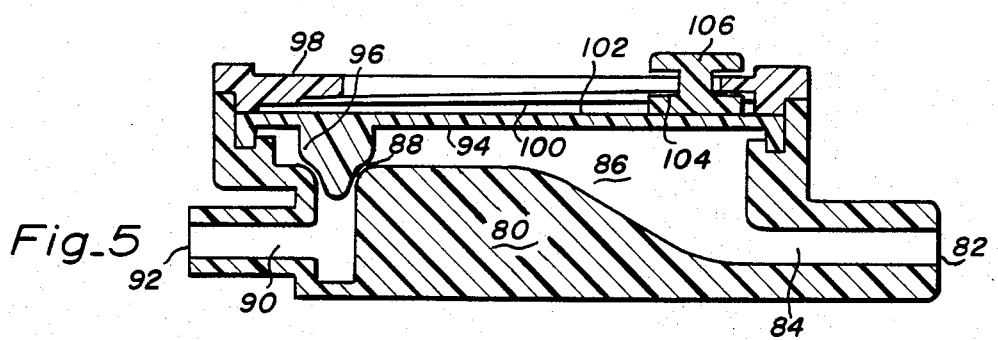
Fig_5

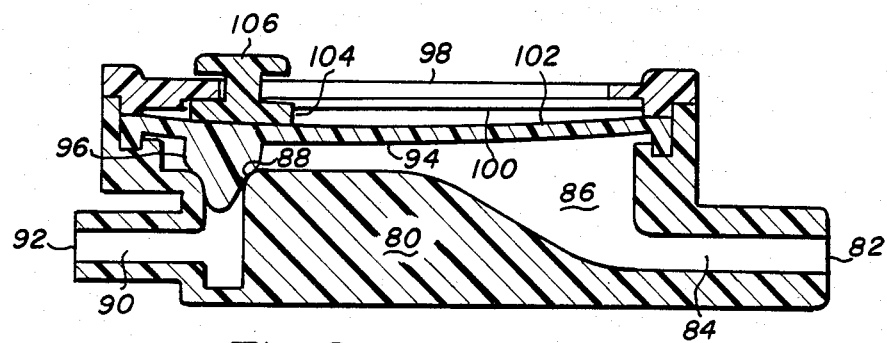
Fig_6
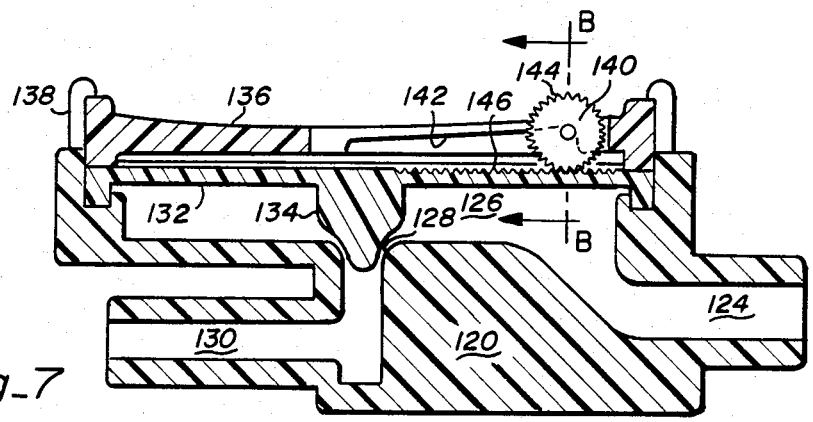
Fig_7
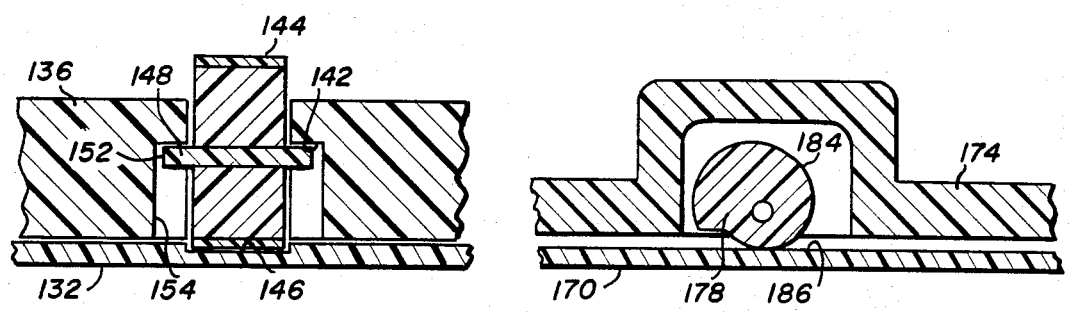
Fig_8      Fig_10
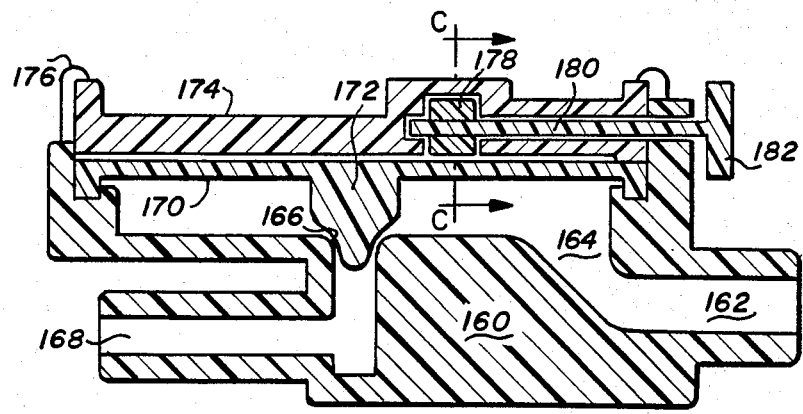
Fig_9

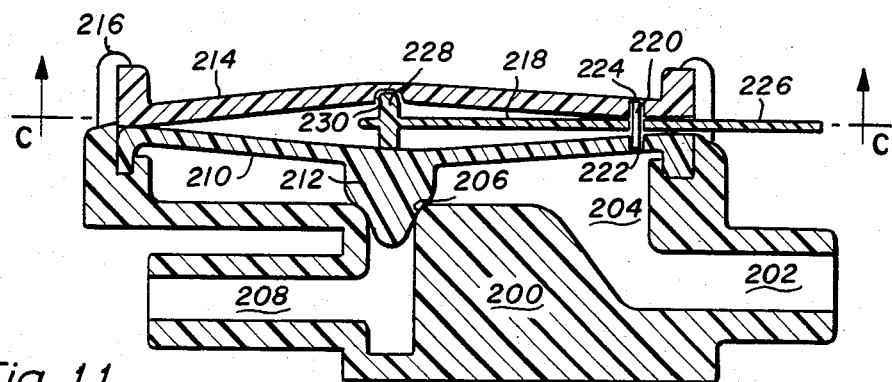
Fig_11
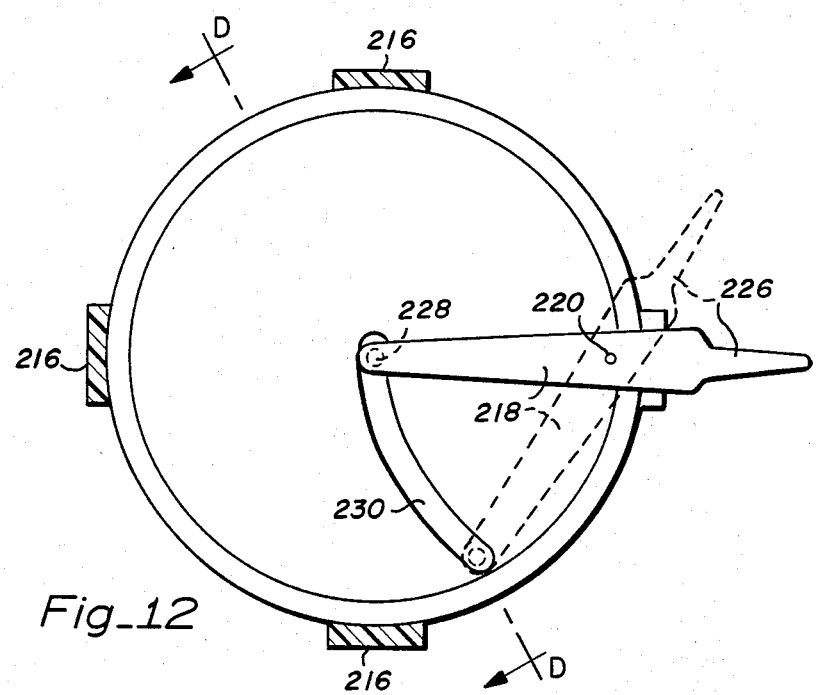
Fig_12
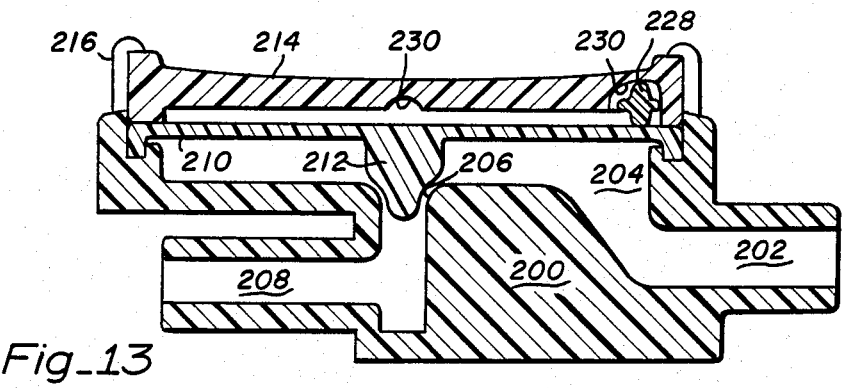
Fig_13

PRECISION VALVE ASSEMBLY

BACKGROUND OF THE INVENTION

1. Field of the Invention

This invention relates to a precision valve assembly which can be used for accurately controlling the flow of fluids delivered to a patient. More specifically, it relates to a precision valve assembly which is particularly suitable for use in conjunction with volumetric control monitors used with fluid administration sets to deliver exact amounts of parenteral and other fluids to patients at precise flow rates.

2. Description of the Prior Art

Medical patients in and out of the hospital frequently require continuous administration of parenteral and other fluids, and these must often be infused at precise, controlled flow rates. Traditionally, an attendant has adjusted a pinch clamp mounted on flexible, plastic tubing to provide a desired drop rate. The conformation of this flow passageway of the pinched tubing is not constant and gradually changes due to plastic creep and hoop tension. To compensate for these changes and avoid a variable flow rate, an attendant must periodically readjust the clamp setting to obtain the desired drop rate.

A variety of flow controllers have been devised which adjust the flow rate of parenteral fluids by automatically operating a pinch clamp or other valve assembly in response to drop rate changes as determined by photoelectric methods. Each drop falls through and interrupts a beam of light, the interruptions are counted, and the count is compared with a desired count. Such a counter is disclosed in U.S. Pat. No. 4,014,010, and systems responsive to such a counter are described in U.S. Pat. Nos. 4,204,538 and 4,207,871.

The flow systems and counters disclosed in the above patents require constant adjustment because of the limitations of the valve assembly, making necessary a large electric energy supply. Portable units are then unduly bulky because of the large battery size. The prior art units tend to be heavy, complex and require operating voltages which are undesirable in a hospital environment, further detracting from their usefulness, particularly as applied to ambulatory patients.

U.S. Pat. No. 3,396,939 discloses a valve structure incorporating a frustuconical member which seats on a valve seat in response to the rotation of portions of the valve assembly. U.S. Pat. No. 2,806,654 discloses a control valve including ball elements. The balls travel in radial tracks and activate a snap action mechanism which in turn drives a valve member to a closed position. These patents are directed to off-on valves used in high pressure systems.

SUMMARY AND OBJECTS OF THE INVENTION

It is an object of this invention to provide a precision valve assembly which is compact, provides a more precise control of fluid therethrough using a minimal amount of energy, and is suitable for use in parenteral infusion systems in a hospital environment.

It is a further object of this invention to provide a lightweight, inexpensive, disposable precision control valve assembly which can be operated either manually or in automatic systems for fluid infusion in a hospital environment.

In summary, the precision valve assembly of this invention comprises first and second valve elements, one of which is a valve and the other is a valve seat aligned therewith. The first valve element is joined to a diaphragm and is movable therewith. The assembly also includes an adjustable actuation means contacting the surface of the diaphragm between the axis of the valve element and adjacent the edge of the diaphragm for flexing the diaphragm and the first valve element mounted thereon in the direction of the second valve element. Preferably, the first valve element is concentric with the central axis of a circular diaphragm, and the point of actuation means contact with the diaphragm is within a zone from its center to adjacent its outer edge. In one embodiment, a backstop means faces the side of the diaphragm opposite the side on which the first valve element is mounted, and the actuator means is positioned between them, contacting the opposed surfaces thereof. The actuator means by pressing the surfaces of the diaphragm and backstop means apart, flexes the diaphragm in a direction away from the backstop means and displaces the first valve element mounted thereon toward the second valve element.

Preferably, the surface of the backstop means facing the diaphragm is sloped and the distance between it and the diaphragm is smallest nearest the axis of the first valve element and gradually increases in a direction away from the axis of the first valve element. With this configuration, movement of the actuator in the direction toward the axis of the first valve element flexes the diaphragm and displaces the first valve element mounted thereon toward the second valve element. With this construction, the actuator can be moved using a screw means. Alternatively, a slide means can be provided having an actuator portion positioned between the diaphragm and the backstop means and having an external projection for manipulation of the slide. In a still further configuration, an adjustment wheel actuator is provided, one rim surface of which engages the diaphragm and the opposite rim surface of which is an external projection means for manipulation of the wheel. The wheel has axle projections contacting the surface of the backstop means opposed to (i.e., facing) the diaphragm. Rotation of the wheel in a direction causing wheel movement toward the axis of the first valve element flexes the diaphragm.

In a still further embodiment, the actuator is a cam means rotatably mounted between the backstop means and diaphragm. Rotation of the cam in one direction increases the distance between the backstop means and diaphragm, thereby flexing the diaphragm and effecting displacement of the first valve element mounted on the diaphragm in the direction of the second valve element.

Still further objects and important aspect of the precision valve assembly of this invention will be apparent from the detailed description provided hereinafter.

BRIEF DESCRIPTION OF THE DRAWINGS

FIG. 1 is a cross-sectional view of a precision valve assembly of this invention having a screw-driven actuator, the device shown in the open position.

FIG. 2 is a cross-sectional view of the precision valve assembly shown in FIG. 1, illustrating the configuration in the closed position.

FIG. 3 is a cross-sectional view of the precision valve assembly of this invention having a slide actuator means.

FIG. 4 is a partial cross-sectional view of the precision valve assembly shown in FIG. 3, taken along lines A—A in FIG. 3.

FIG. 5 is a cross-sectional view of the precision valve assembly of this invention with non-circular diaphragm and inflexible element configurations, and with a slide acutator means, shown in the open position.

FIG. 6 is a cross-sectional view of the precision valve assembly shown in FIG. 5, illustrating the configuration in the closed position.

FIG. 7 is a cross-sectional view of a precision valve assembly of this invention having a wheel actuator.

FIG. 8 is a partial cross-sectional view of the precision valve assembly shown in FIG. 7, taken along lines B—B in FIG. 7.

FIG. 9 is a cross-sectional view of a precision valve assembly of this invention with a cam actuator.

FIG. 10 is a partial cross-sectional view of the precision valve assembly shown in FIG. 9, taken along lines C—C in FIG. 9.

FIG. 11 is a cross-sectional view of a lever operated embodiment of the precision valve assembly of this invention.

FIG. 12 is a cross-sectional view of the precision valve assembly taken along the lines C—C in FIG. 11.

FIG. 13 is a cross-sectional view of the precision valve assembly taken along the lines D—D in FIG. 12.

DESCRIPTION OF THE PREFERRED EMBODIMENTS

Referring to FIGS. 1 and 2, cross-sectional views of the precision valve assembly of this invention having a screw driven actuator are shown. The valve assembly housing 2 has an inlet opening 4 and inlet passageway 5 communicating with a central chamber 6. The valve seat 8 is the outlet of the chamber 6 and communicates with the outlet passageway 10 terminating in the outlet opening 12. The circular diaphragm 14 has a valve element 16 joined at its center. In the embodiment shown, the diaphragm 14 and valve 16 are formed in a unitary construction. However, they can be separately formed and joined by adhesives, solvent bonding or welding.

The backstop element 18 is opposed to the diaphragm 14, facing the surface thereof opposite the valve element 16. It is held in place against the housing 2 by the snap fasteners 20 projecting from the valve assembly housing 2. The thickness of the backstop means is greatest near its outer edges, gradually decreasing toward its axial center so that its flexibility is increased toward its center.

The actuator 22 is positioned between the backstop means 18 and diaphragm 14. The position of the actuator is controlled by the threaded stem 24 attached thereto, which threaded stem cooperates with the threaded hole 26 in the backstop means. The knurled knob 28, when rotated, turns the threaded stem 24 and effects translation of the actuator 22 from the position remote from the valve 16 (shown in FIG. 1) to a position closer thereto (shown in FIG. 2).

A portion 30 of the surface of the backstop means 18 opposed to the diaphragm surface 32 has a tapered configuration such that the distance between the backstop means element surface 30 and the diaphragm surface 32 is smaller proximate the valve element 16 and is greater adjacent its rim. These opposed surfaces form a wedge-shaped space. The actuator 22 contacts both surfaces 30 and 32 and its position determines the amount of deflection (or flexing) of the diaphragm 14 in a direction away from the backstop means 18. The flexing movement of the diaphragm, through a leverage action, displaces the valve 16 toward the valve seat 8 and effects a restriction or closure of the space therebetween.

Referring to FIG. 2, the device shown in FIG. 1 is illustrated with the actuator in a position which effectively closes space between the valve 16 and valve seat 8, thereby closing the valve. By comparing the actuator position in FIGS. 1 and 2 and observing the degree of deflection of the diaphragm surface 32 in a position away from the backstop means 18, the leverage action effected by the actuator 22 can be seen. Continued rotation of the actuator screw 24, advancing the actuator nearer the axis of the valve 16 and increasing the pressure between the valve and valve seat, causes flexing of the backstop member 18 in a direction away from the diaphragm, thereby relieving the system from excessive strain. Having the flexibility of the backstop member greatest adjacent the axis of the valve elements improves the strain relief. Actuator 22 can also be made of elastic material such as an elastomeric organic polymer, which by elastic deformation under compressive strain, relieves strain.

Referring to FIGS. 3 and 4, a cross-sectional view of a precision valve assembly of this invention is shown having a slide actuator means. In this embodiment, a valve assembly housing 40 has an inlet passageway 42 opening into a central chamber 44. The valve seat 46 is the outlet opening of the open chamber 44 and is connected by outlet passageway 48 with the outlet opening 50. The circular diaphragm 52 has a valve 54 at the axial center thereof. The backstop means 56 is held in place against the valve assembly housing 40 by the snap fasteners 58.

Slide actuator 60 is unitary with the projection 62 provided for manipulation of the slide.

Referring to FIG. 4, a partial cross-sectional view of the device shown in FIG. 3 taken along the lines A—A is shown. From this view, it can be seen that the projection 62 provided for manipulation is joined to the slide actuator 60 by the slide stem 68. The actuator shoulder 70 bears against a groove surface 64 in the inflexible element 56. Viewing this construction in conjunction with FIG. 3, one can see that the groove surface 64 is tapered and is closer to the circular diaphragm 52 near its center than near its outer edge. Movement of the slide actuator 60 in translation toward the center of the diaphragm causes the slide surface 70 to bear against the shoulder 64, depressing the slide 60 and displacing (flexing) the diaphragm surface 66 opposed thereto. This effects a flexing displacement of the diaphragm 52 and corresponding displacement of the valve 54 toward the valve seat 46. The grooved surface 74 in the inflexible element 56 bears against the lateral surface 76 of the slide 60, thereby guiding its translational motion.

Another embodiment of the precision valve assembly of this invention with non-circular diaphragm and inflexible element configurations is shown in FIGS. 5 and 6. The valve assembly housing 80 has an inlet opening communicating with inlet passageway 84 leading to the chamber 86. The valve seat 88 is the outlet opening of the chamber 86 and communicates with the outlet passageway 90 leading to the outlet opening 92. The diaphragm 94 has the valve 96 joined thereto. In this embodiment, the diaphragm 94 and valve 96 are shown as a unitary construction, but they can be separately formed and joined by the use of adhesives, solvent bonding, welding and the like. The backstop means 98 is joined to the valve assembly housing 80 by adhesives, solvent bonding, welding or the like. The backstop means 98 has a tapered surface 100 against which the slide actuator 104 bears. The distance between the tapered surface 100 and the opposed diaphragm surface 102 is smallest near the valve element 96, and gradually increases in the direction away from the valve element 96. The slide 104 has a projection 106 for manipulation joined thereto. Details of the construction are essentially the same as those shown in the partial cross-sectional view shown in FIG. 4. Referring to FIG. 6, the flexing of the diaphragm 94 which occurs as a result of the movement of the slide 104 to a position nearest the valve element 96 can be seen. As the slide approaches the valve element 96, the backstop means surface 100 displaces the slide 104 in the direction of the diaphragm 94, depressing the diaphragm. This creates a leverage action which further moves the valve element 96 toward the valve seat 88. The backstop member 98, by flexing away from the diaphragm 94 above the actuator 104 relieves strain.

Referring to FIGS. 7 and 8, an embodiment of the precision valve assembly of this invention having a wheel actuator is shown. The valve assembly housing 120 has an inlet passageway 124 communicating with the central chamber 126. Valve seat 128 in the central chamber 126 is the outlet opening thereof and communicates with the outlet passageway 130. Circular diaphragm 132 has, at its center, the valve 134. The backstop means 136 is held against the valve assembly housing 120 by the snap fasteners 138. The actuator wheel 140 cooperates with the tapered backstop means surface 142 to control the opening between the valve 134 and the valve seat 128. The actuator wheel rim has cogs or toothed projections 144 in its surface which cooperate with flutes or grooves 146 in the diaphragm surface. These not only provide a positive, non-slipping engagement between the surfaces 140 and 146 but facilitate friction for manipulation of the wheel 140.

Referring to FIG. 8, a partial cross-sectional view of the device shown in FIG. 7 taken along lines B—B is shown to further illustrate the wheel actuator mechanisms. The wheel 140 has an axle 148. When the wheel 140 is rolled toward the valve 134, the surface of the axle 148 bears against the tapered backstop means surface 142, and the wheel surface 144 presses against the diaphragm surface 146, depressing it. This flexing depression, by lever action, moves the valve 134 toward the valve seat 128. The axle ends 152 bear against the lateral surface 154 of the backstop means, guiding the wheel.

In the embodiments of the invention shown in FIGS. 1-8, motion of the actuator from a distant position with respect to the valve to a position near the valve effects valve movement toward a closed position. Movement of the actuator means in an opposite direction permits a reverse diaphragm motion, effecting an opening movement of the valve. Positioning the actuator at any position between the operating extremes provides a corresponding degree of valve opening restriction in a gradual manner, permitting a very precise valve opening adjustment. A substantial actuator movement is thus translated to a small valve movement, a major control advantage.

Referring to FIGS. 9 and 10, an embodiment of the precision valve assembly of this invention is shown having a cam actuator. The valve assembly housing 160 has an inlet passageway 162 communicating with the chamber 164. The valve seat 166 communicates with the chamber 164 and is the outlet opening thereof leading to the outlet passageway 168. The circular diaphragm 170 has a valve element 172 in the center thereof. The backstop means 174 is held against the valve assembly housing 160 by the snap fasteners 176. An actuator cam 178 is driven by a drive stem 180 connected with the drive wheel 182.

Referring to FIG. 10, a cross-sectional view of the actuator cam assembly taken along the lines C—C in FIG. 9 is shown. The cam surface 184 bears against the diaphragm surface 186. Clockwise rotation of the cam 178 (in the view of FIG. 10) flexes the diaphragm surface 186 and displaces it. This leverages the diaphragm 170 and the valve 172 mounted thereon in the direction toward the valve seat 166. Counterclockwise rotation of the cam 178 permits return of the diaphragm 170 toward its original position and permits the valve element 172 to move away from the valve seat 166.

Referring to FIGS. 11-13, a still further embodiment of this invention is shown. FIG. 11 shows a cross-sectional side view. The valve assembly housing 200 has an inlet passageway 202 leading to a chamber 204. Valve seat 206 is an outlet therefrom leading to outlet passageway 208. Circular diaphragm element 210 has a valve 212 mounted axially concentric therewith. Backstop member 214 is held in position with respect to the diaphragm 210 by snap fasteners 216.

The actuator means comprises a lever 218 pivoted about pin 220 held in pivot holes 222 and 224 in the diaphragm and backstop members, respectively. At one end of the lever 218 is the manipulation arm 226 and at the other end is an actuator projection or slide 228. The actuator projection 228 in the position shown in FIG. 11 is pressing the diaphragm and the valve 212 to the closed position, and the backstop member 214, being more flexible at its center, is flexed in a direction away from the diaphragm to relieve stress on the valve members. The zone of backstop member 214 contacted by projection 228 in moving from the closed valve position to the open valve position is an arcuate path 230 having a sloped surface.

FIG. 12 is a cross-sectional view taken along the lines C—C of FIG. 11. FIG. 12 shows the arcuate path 230 of the backstop member 214 with the actuator means in the closed position. A dotted representation of the actuator lever 218 in the "open position" is also shown. The surface 230 gradually slopes toward the diaphragm 210 so that the distance between the diaphragm 210 and the surface 230 is smallest adjacent the central axis of the diaphragm and largest adjacent the outer periphery thereof in the unflexed configuration when the valve is maximally open.

FIG. 13 is a cross-sectional view of the valve assembly in the "open position" taken along the lines D—D of FIG. 12. With the actuator projection or slide 228 in the position adjacent the outer periphery of the diaphragm (the dotted line position shown in FIG. 12), the diaphragm 210 and backstop member 214 are in the unflexed position, and the valve elements 212 and 206 are maximally open.

The above described valve components can be made of standard materials of construction. They are preferably made of plastic and can be made of thermoplastic material which can be injection molded. Suitable plastics for the construction of the valve assembly housing and diaphragm include acetal polymers and copolymers, nylon, polycarbonates, high density polyethylene, polypropylene, and the like. The actuator can be made of the same material as the valve assembly housing or a different elastic polymeric material such as polybutadiene, natural rubber, silicone rubber or the like.

The invention claimed is:

1. A precision valve assembly comprising first and second valve elements, one of which is a valve and the other is a valve seat aligned therewith, the first valve element being joined to a diaphragm having first and second opposite surfaces and movable therewith, the first valve element projecting from the first surface of the diaphragm, an adjustable actuation means contacting the second surface of the diaphragm between the axis of the valve element and adjacent the edge of the diaphragm for flexing the diaphragm and displacing the first valve element toward the second valve element, a backstop means facing the second surface of the diaphragm and the actuator means positioned in contacting engagement between the backstop means and the second surface of the diaphragm, whereby movement of the actuator means pressing the surfaces of the diaphragm and backstop means apart flexes the diaphragm in a direction away from the backstop means and displaces the first valve element toward the second valve means, wherein the backstop means is less flexible than the diaphragm but sufficiently flexible to relieve pressure on the diaphragm resulting from actuator movement continued after the first and second valve elements are maximally closed.

2. The precision valve assembly of claim 1 wherein the flexibility of the backstop means is greatest adjacent the axis of the first valve element and gradually decreases in a direction away from said axis.

3. A precision valve assembly comprising first and second valve elements, one of which is a valve and the other is a valve seat aligned therewith, the first valve element being joined to a diaphragm having first and second opposite surfaces and movable therewith, the first valve element projecting from the first surface of the diaphragm, an adjustable actuation means contacting the second surface of the diaphragm between the axis of the valve element and adjacent the edge of the diaphragm for flexing the diaphragm and displacing the first valve element toward the second valve element, a backstop means facing the second surface of the diaphragm and the actuator means is positioned in contacting engagement between the backstop means and the second surface of the diaphragm, whereby movement of the actuator means pressing the surfaces of the diaphragm and backstop means apart flexes the diaphragm in a direction away from the backstop means and displaces the first valve element toward the second valve means, wherein the actuator means comprises an elastic strain relief means.

4. A precision valve assembly comprising first and second valve elements, one of which is a valve and the other is a valve seat aligned therewith, the first valve element being joined to a diaphragm having first and second opposite surfaces and movable therewith, the first valve element projecting from the first surface of the diaphragm, an adjustable actuation means contacting the second surface of the diaphragm between the axis of the valve element and adjacent the edge of the diaphragm for flexing the diaphragm and displacing the first valve element element toward the second valve element, a backstop means facing the second surface of the diaphragm and the actuator means is positioned in contacting engagement between the backstop means and the second surface of the diaphragm, whereby movement of the actuator means pressing the surfaces of the diaphragm and backstop means apart flexes the diaphragm in a direction away from the backstop means and displaces the first valve element toward the second valve element, the distance between at least a portion of the backstop means and the second diaphragm surface being smallest nearest the axis of the first valve element and gradually increasing in a direction away from said axis of the first valve element, whereby movement of the actuator in the direction toward the axis of the first valve element flexes the diaphragm and displaces the first valve element mounted thereon toward the second valve element, the actuator including a lever pivoted about a point at a distance from the axis of the first valve element, the lever having a slide means at one end and an external projection for manipulation at the other end, whereby pivotal movement of the lever moves the slide means in an arcuate path between the backstop means and second diaphragm surface to flex the diaphragm.

5. A precision valve assembly comprising first and second valve elements, one of which is a valve and the other is a valve seat aligned therewith, the first valve element being joined to a diaphragm having first and second opposite surfaces and movable therewith, the first valve element projecting from the first surface of the diaphragm, an adjustable actuation means contacting the second surface of the diaphragm between the axis of the valve element and adjacent the edge of the diaphragm for flexing the diaphragm and displacing the first valve element toward the second valve element, a backstop means facing the second surface of the diaphragm, the actuator means being positioned in contacting engagement with the backstop means and the second surface of the diaphragm, whereby movement of the actuator means pressing the surfaces of the diaphragm and backstop means apart flexes the diaphragm in a direction away from the backstop means and displaces the first valve element toward the second valve element, the backstop means being less flexible than the diaphragm but sufficiently flexible to relieve pressure on the diaphragm by actuator movement continued after the first and second valve elements are maximally closed.

6. The precision valve assembly of claim 5 wherein the tip of the actuator means is a resilient material comprising an elastic strain relief means.

7. A precision valve assembly comprising first and second valve elements, one of which is a valve and the other is a valve seat aligned therewith, the first valve element being joined to a diaphragm having first and second opposite surfaces and movable therewith, the first valve element projecting from the first surface of the diaphragm, an adjustable actuation means contacting the second surface of the diaphragm between the axis of the valve element and adjacent the edge of the diaphragm for flexing the diaphragm and displacing the first valve element toward the second valve element, a backstop means facing the second surface of the diaphragm, the actuator means being positioned in contacting engagement with the backstop means and the second surface of the diaphragm, whereby movement of the actuator means pressing the surfaces of the diaphragm and backstop means apart flexes the diaphragm in a direction away from the backstop means and displaces the first valve element toward the second valve element, the distance between at least a portion of the backstop means and the second diaphragm surface being smallest nearest the axis of the first valve element and gradually increasing in a direction away from said axis of the first valve element, whereby movement of the actuator in the direction toward the axis of the first valve element flexes the diaphragm and displaces the first valve element mounted thereon toward the second valve element, the actuator including a lever pivoted about a point at a distance from the axis of the first valve element, the lever having a slide means at one end and an external projection for manipulation at the other end, whereby pivotal movement of the lever moves the slide means in an arcuate path between the backstop means and second diaphragm surface to flex the diaphragm.

* * * * *